United States Patent [19]

Kopelman et al.

[11] Patent Number: 6,099,314

[45] Date of Patent: Aug. 8, 2000

[54] METHOD AND SYSTEM FOR ACQUIRING THREE-DIMENSIONAL TEETH IMAGE

[75] Inventors: Avi Kopelman, Ramat Chen; Eldad Taub, Reut, both of Israel

[73] Assignee: Cadent Ltd., Or Yehuda, Israel

[21] Appl. No.: 09/000,036

[22] PCT Filed: Jul. 4, 1996

[86] PCT No.: PCT/IL96/00036

§ 371 Date: Jan. 20, 1998

§ 102(e) Date: Jan. 20, 1998

[87] PCT Pub. No.: WO97/03622

PCT Pub. Date: Feb. 6, 1997

[30] Foreign Application Priority Data

Jul. 21, 1995 [IL] Israel ............................................ 114691
May 31, 1996 [IL] Israel ............................................ 118523

[51] Int. Cl.[7] .................................................. A61C 9/00
[52] U.S. Cl. ........................................... 433/213; 433/214
[58] Field of Search .................................. 433/214, 213, 433/37, 48

[56] References Cited

U.S. PATENT DOCUMENTS

| | | | |
|---|---|---|---|
| 4,445,854 | 5/1984 | Berkey et al. ............................ | 433/37 |
| 4,935,635 | 6/1990 | O'Harra .................................. | 250/560 |
| 5,018,967 | 5/1991 | Schwalbach .............................. | 433/37 |
| 5,237,998 | 8/1993 | Duret et al. ............................ | 128/665 |

FOREIGN PATENT DOCUMENTS

| | | |
|---|---|---|
| 0 634 150 A1 | 1/1995 | European Pat. Off. . |
| 3810455 A1 | 10/1989 | Germany . |
| C1-41 41311 | 8/1993 | Germany . |
| WO-9424957 | 11/1994 | WIPO . |

OTHER PUBLICATIONS

Laurendeau, Denis et al., "A Computer–Vision Technique for the Acquisition and Processing of 3–D Profiles of Dental Imprints: An Application in Orthodontics", *IEEE Transactions on Medical Imaging*, 10 (1991) Sep. No. 3, New York, 453–461.

*Primary Examiner*—John J. Wilson
*Attorney, Agent, or Firm*—Oliff & Berridge, PLC

[57] ABSTRACT

A method of obtaining a dental image, such as a three-dimensional image of teeth, providing a three-dimensional physical teeth model. The three-dimensional physical teeth model can be either: a negative teeth model that includes a matrix with a plurality of cavities or recesses, each corresponding to a tooth; or a positive teeth model, that includes a matrix with a plurality of projections or bulges, each corresponding to a tooth. The method also includes removing a portion of the model in a controlled, step-wise manner, and in each step acquiring an optical image of the model or of its removed portion, digitizing each of the optical images in order to obtain a plurality of digital images, and compiling the plurality of digital images to obtain a three-dimensional digital dental image.

2 Claims, 19 Drawing Sheets

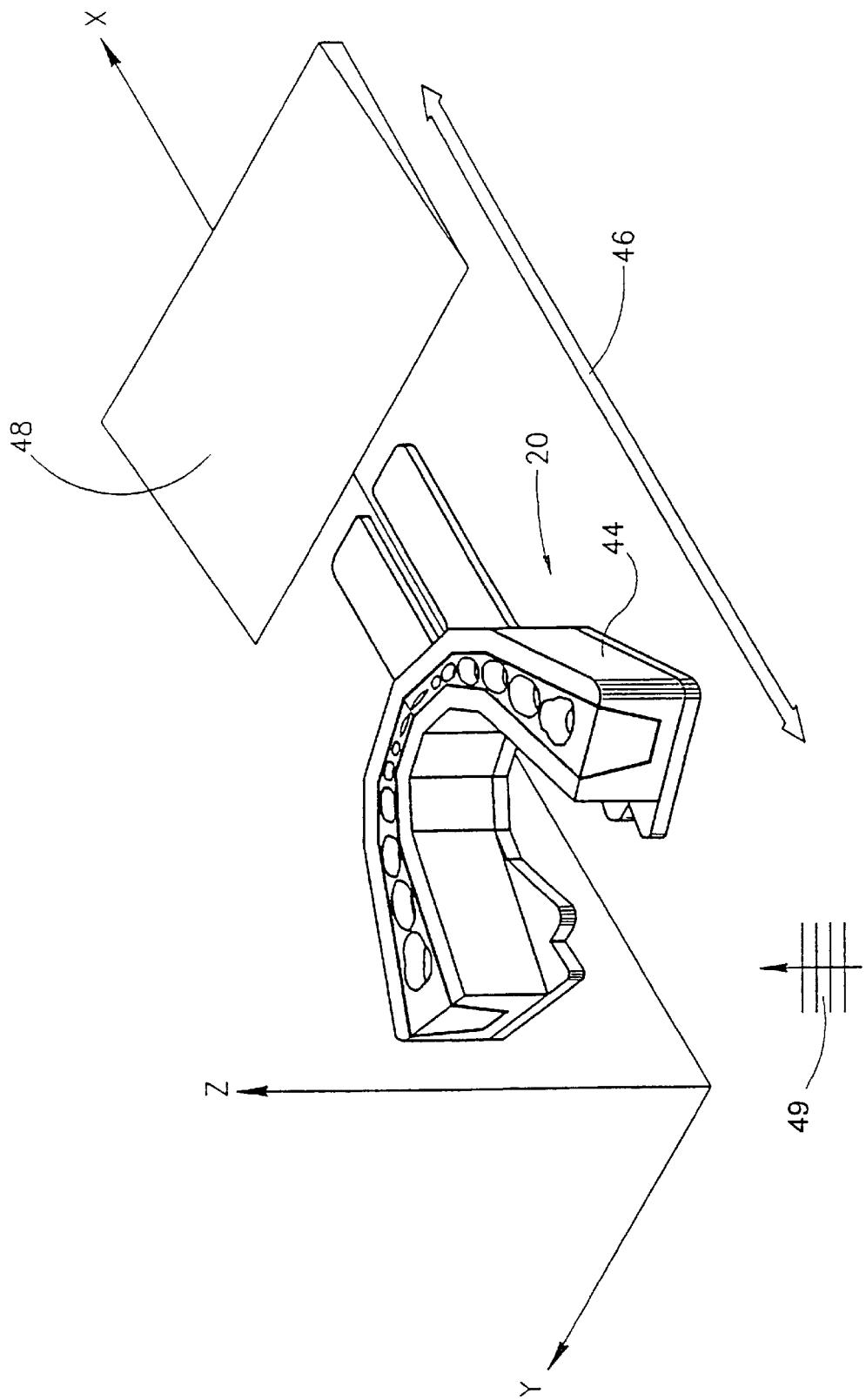

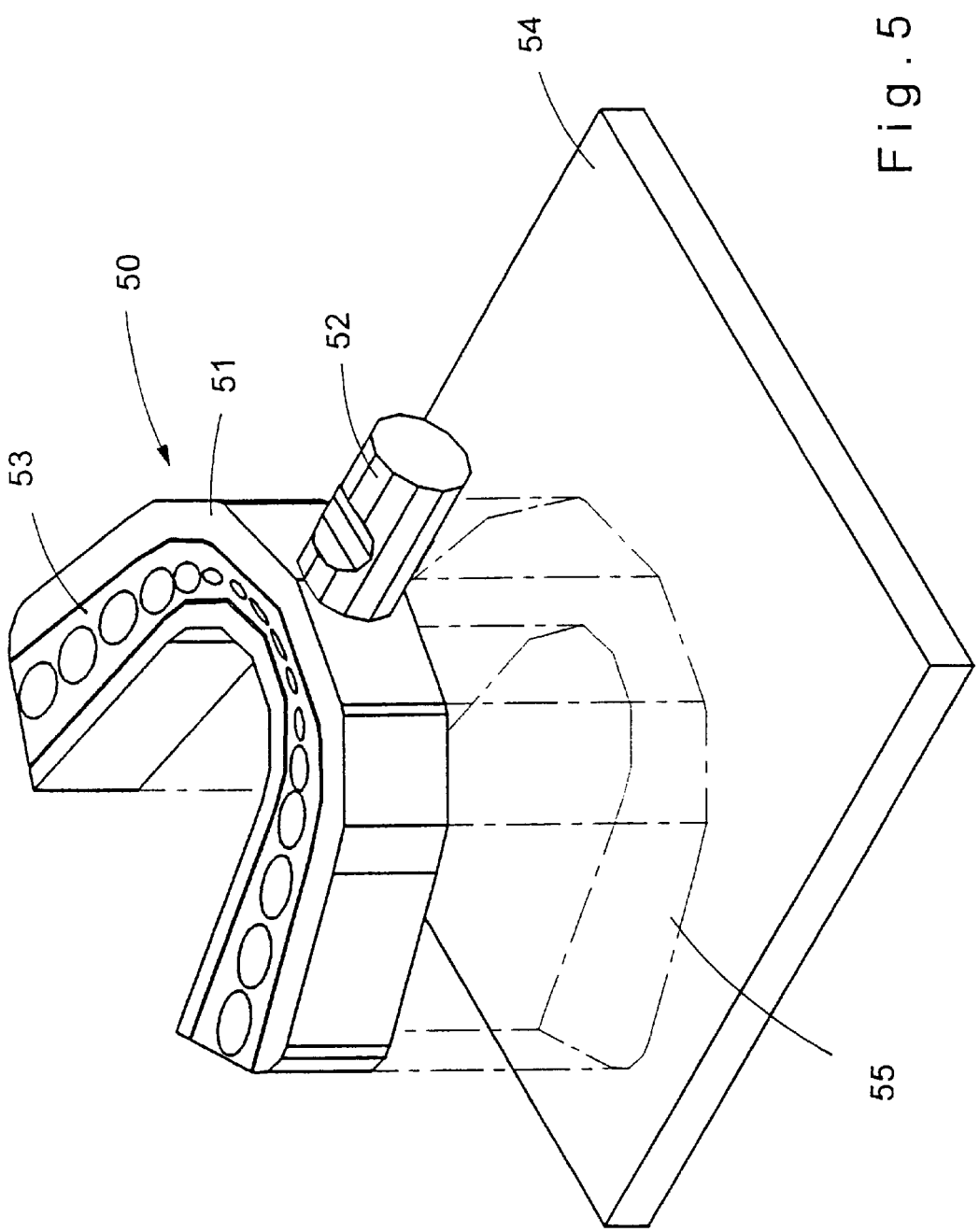

METHOD AND SYSTEM FOR ACQUIRING THREE-DIMENSIONAL TEETH IMAGE

FIELD AND BACKGROUND OF THE INVENTION

The invention is generally in the field of dentistry and concerns a method and system for acquiring a three-dimensional image of teeth geometry. In the following, the term "dental image" will be used to denote an acquired three-dimensional teeth image.

The term "partial dental image" will be used to denote an image of part of the teeth surface, e.g. an image of only the lingual surfaces of the teeth ("lingual image") or of only the buccal surfaces of the teeth ("buccal image"); the term "sectional dental image" will be used to denote an image of a section of the teeth, i.e. not including all the teeth.

The obtaining of a dental image is of importance for various dental, and particularly orthodontic procedures in order to make treatment decisions, e.g. design braces, crowns or the like, and to allow monitoring of an orthodontal treatment. Typically, in accordance with existing methods, a teeth impression in an appropriate matrix is obtained and from that a positive, typically plaster, teeth model is prepared. Such a teeth model can be stored as such, it can be photographed, it can be scanned and stored digitally in a computer, etc. Scanning and digitizing a three-dimensional teeth image is a relatively complex procedure. Various methods have been proposed involving direct scanning of teeth by probes which forms part of an imaging system fixed to the skull, but such procedures cannot easily be practiced in widespread use.

DE-A1-3810455, published on Oct. 5, 1989, discloses a system for acquiring a three-dimensional image of an irregular object, particularly teeth, which comprises an optic system consisting of an illuminator and an optical receiver, by scanning the teeth with the optic system, a three-dimensional image is obtained.

U.S. Pat. No. 4,935,635 of Jan. 19, 1990, discloses a three-dimensional measuring system intended particularly for use in acquiring a three-dimensional teeth object. The system has a laser diode which projects a triangulating beam at the surface of the object to be mapped, the beam scanning repeatedly across the surface. By triangulation, the X-axis, or the depth information is obtained and by correlating a particular point with a position of the scanner along the scan line gives the Y-axis information, i.e. information on the width's direction. The scanner and diode are mounted on a slide or platform which move in a "Y" axis in and out the mouth, driven by a stepper motor, and the monitored position of the stepper motor is coordinated with the other information on each spot to yield X-axis information.

Laurendeau, D., et al., *IEEE Transactions on Medical Imaging,* 10(3):453–461, New York, USA, 1991 discloses a computer vision technique for acquiring and processing of dental images. In accordance with this paper a standard three-dimensional teeth wax image is prepared and is optically scanned simultaneously in both sides whereby three-dimensional teeth image is obtained.

U.S. Pat. No. 5,237,988 of Aug. 24, 1993 discloses a three dimensional correlation of images of dental arcades, making use of an impression in the occlusive position, providing a reference in the form of three mutually spaced reference points. Three-dimensional views are taken of the impression and the points and views are also taken with the impression removed. Using the images of the reference points as a basis, the sets of views are then correlated to bring them into a single reference system.

EP-A1-634150 published on Jan. 18, 1995, discloses an aid for the production of a tooth or bridge. In accordance with this publication, a model is placed on a rotary holder and during rotation is scanned by an angled scanning device.

GENERAL DESCRIPTION OF THE INVENTION

It is an object of the invention to provide a novel method for acquiring a dental image.

It is another object of the invention to provide a system for acquiring a dental image.

It is furthermore an object of the invention to provide a tool for obtaining a teeth impression useful in the above method and system.

In the following text, the term "teeth model" will be used to denote a physical, three-dimensional representation of teeth in a solid matrix. Such a model may be a "positive teeth model" comprising a teeth replica, namely a model where each tooth is represented by a projection or bulge having contours identical in size and shape to the corresponding tooth; or maybe a "negative teeth model" where each tooth is represented by a cavity or recess with contours identical in size but opposite in shape to the contours of the corresponding tooth.

The present invention arises out of a novel and unique concept for obtaining a three-dimensional computerized teeth image. In accordance with the invention, a physical, three-dimensional teeth model is first prepared and is then subjected to a controlled destruction, proceeding in a step-wise manner, where in each step a portion of the model is removed. In each such step an image is taken of either the removed portion or of the remainder of the model, thus obtaining a plurality of sequential digital images. Then, by a proper combination of the sequential digital images, based, inter alia, on parameters relating to the relations between the different sequential images, a three-dimensional digital image of the teeth is then obtained.

The invention provides, by a first of its aspects, a method for obtaining a dental image, being a three-dimensional image of teeth, the method comprising:

(a) providing a three-dimensional physical teeth model, being either a negative teeth model comprising a matrix with a plurality of cavities or recesses, each corresponding to a tooth, or a positive teeth model, comprising a matrix with a plurality of projections or bulges, each corresponding to a tooth;

(b) removing portions of the model in a controlled, step-wise manner, and in each step acquiring a step optical image of the model or of their removed portion, digitizing each of the step optical images to obtain a plurality of digital images; and (c) compiling the plurality of digital images to obtain a three-dimensional digital dental image.

The present invention further provides a method for obtaining a dental image which comprises:

(a) providing a physical teeth model, being either a negative teeth model comprising a matrix with a plurality of cavities or recesses with boundaries corresponding to boundaries of the teeth, or a positive teeth model comprising a matrix with a plurality of projections or bulges with boundaries corresponding to boundaries of the teeth;

(b) removing a layer portion off a face of choice so as to obtain a flat, surface, and acquiring a first, two-dimensional digital image of the flat surface or of the removed portion;

(c) removing another layer portion off the chosen face so as to obtain a new, flat surface and acquire a consecutive two-dimensional digital image of the new flat surface or of the removed portion;

(d) repeating step (c) a plurality of times until removal of sufficient layer portions of the teeth model to allow the obtaining of a dental image;

(e) determining boundaries of the cavities or recesses in the case of the negative teeth model or boundaries of the projections or bulges in the case of the positive tooth model in the first image and in each of the consecutive images to obtain a plurality of boundaries representations of the first and subsequent images;

(f) combining at least some of the boundaries' representations into a three-dimensional digital dental image.

In accordance with the invention, a negative teeth model comprising the teeth impression is first prepared by dentists, dental technicians, etc. A matrix in which a teeth impression is obtained will be referred to herein as "impression matrix". This negative teeth model may be used in the method as such, or may alternatively be used to prepare a positive teeth image. In accordance with the method of the present invention, use of a negative teeth model is currently a preferred embodiment, although use of a positive teeth model is also a feasible embodiment of the invention. In the following, the invention will in described primarily in relation to the use of a negative teeth model, although it will be appreciated by the artisan that in a similar manner, mutatis mutandis, the invention may also be practiced using a positive teeth model.

After a teeth model is prepared, the model is first processed to obtain an initial flat surface on one of the faces of the model ("face of choice"). The face of choice may be the face corresponding to the teeth apex or the teeth base, i.e. having a horizontal orientation relative to the general orientation of the teeth model. The face of choice may also be vertical at one of the side, rear or front faces of the model and furthermore, may also have an intermediate orientation between either the aforementioned horizontal or vertical orientations of the model, namely, an oblique orientation.

After acquiring a first image, a subsequent layer portion is removed and an image is acquired again. Typically, the portion which will be removed would be such that the subsequent exposed flat surface is parallel to the previous surface. However, this is not essential and it is possible by some embodiments of the invention, to process the model in a manner that consecutive exposed flat surfaces will have a slightly different, oblique orientation vis-vis one another.

The images of the different flat surfaces will provide, for each such surface, the boundaries of the cavities or recesses or the boundaries of the projection or bulges, as the case may be. On the basis of known parameters relating to the thickness of each removed layer (and where each flat surface has a slightly different orientation than the previous one, also on the basis of known parameters regarding such change of orientation) and by computerized combination of consecutive images, an entire three-dimensional digital image of the teeth may be obtained.

The process of removing a layer, acquiring an image of the obtained flat surface, etc. may be preceded to a depth so as to process the entire model in this way. However, at times, it may not be necessary to proceed to such a depth and the process may be terminated after sufficient layers have been removed. This may be the case, for example, where it is desired to model only the teeth apex or only the teeth base; or where the layer portion removal precedes from a side of the model, until a depth so as to cover entire teeth section has been reached, etc.

In accordance with the above preferred embodiment (where the three-dimensional image is obtained by processing a negative teeth model), in order to allow better viewing the boundaries, the walls of the cavities or recesses which were impressed by the teeth in the impression matrix, may be colored by a contrasting color, or alternatively, the cavities and recesses may be filled by a dye or an appropriately colored curable substance (the color of the curable substance should be different than the color of the impression matrix so as to allow clear viewing of the boundaries). The curable substance, once cured, should preferably have essentially the same degree of hardness as the impression matrix.

In accordance with another embodiment of the invention, rather than acquiring planar images of either the negative teeth model or of the positive teeth model, the slices may be carefully removed and an image of the slices is then acquired.

The image acquired by the system may be a complete dental image or may be a partial dental image, e.g. a lingual image or a buccal image. Furthermore, the image acquired may also be a dental image of a teeth section, e.g. the upper right or upper left, or it may be an image of all teeth of the section in their entirety, or only a sectional image, etc.

It should be noted that in order to obtain an accurate dental image, the layers removed in each step should be relatively thin, e.g. about 0.05–0.2 mm.

As will be appreciated, step (e) in the above method (the second defined method) which is the step of boundary determination, can be performed either at essentially real time immediately after image acquisition or can be performed at a later time after acquiring all of the images.

In accordance with another aspect of the present invention, there is provided a system for obtaining a dental image. The system comprises:

(a) holders of a teeth model;

(b) a cutting tool for removing successive thin slices of the matrix;

(c) an imaging device for acquiring successive two-dimensional elevational images of either said matrix or of slices removed therefrom, and digitizing the acquired images;

(d) a processor for combining a plurality of successive digitized acquired images into a three-dimensional digital dental image.

In accordance with the present invention, use is preferably made with a novel tool for obtaining a teeth impression and for holding the matrix containing the teeth impression while slices are removed therefrom in said system. While the use of this tool within the framework of the above methods and system is a preferred embodiment of the methods and system, it also forms an independent aspect of the present invention. This tool comprises a matrix retainer having a recess for holding an impression matrix, the recess having a general shape allowing immersion of teeth or portions thereof in the impression matrix so as to form a negative teeth impression in the matrix, said matrix retainer being made of a substance which can be cut by a cutting tool capable of cutting the matrix. In accordance with one embodiment of the present invention, the tool in-its entirety, or at least the matrix retainer is made of a substance which can be cut by the cutting tool. Such a substance, may for example, be styrofoam (polystyene foam). In other embodiments, the tool comprises a rigid base with the matrix retainer being fixed on the base. Tools comprising a rigid base are useful where the step-wise layer portion removal is in an orientation which is parallel to the base.

The matrix retainer may be designed to allow obtaining of a complete teeth impression. It is also possible to design the matrix retainer to obtain a partial teeth impression, e.g. an impression of only the lingual or only the buccal surfaces of the teeth. Furthermore, the matrix retainer may also be designed to obtain only a sectional dental impression.

In accordance with an embodiment of the invention, the base holds two matrix retainers, fixed on opposite sides thereof, for simultaneously obtaining of a dental image of teeth of both the upper and the lower jaws.

In the following, the invention will be illustrated with reference to some specific, non-limiting embodiments, with occasional reference to the annexed drawings.

BRIEF DESCRIPTION OF THE DRAWINGS

In the drawings:

FIG. 4A is a schematic representation of the manner of slicing off horizontal layers from the block carried on the tool of FIG. 2;

FIG. 5 is an isometric view of a tool in accordance with another embodiment of the invention containing an impression matrix with a teeth impression fixed therein;

DESCRIPTION OF SPECIFIC EMBODIMENTS

Figure 1:
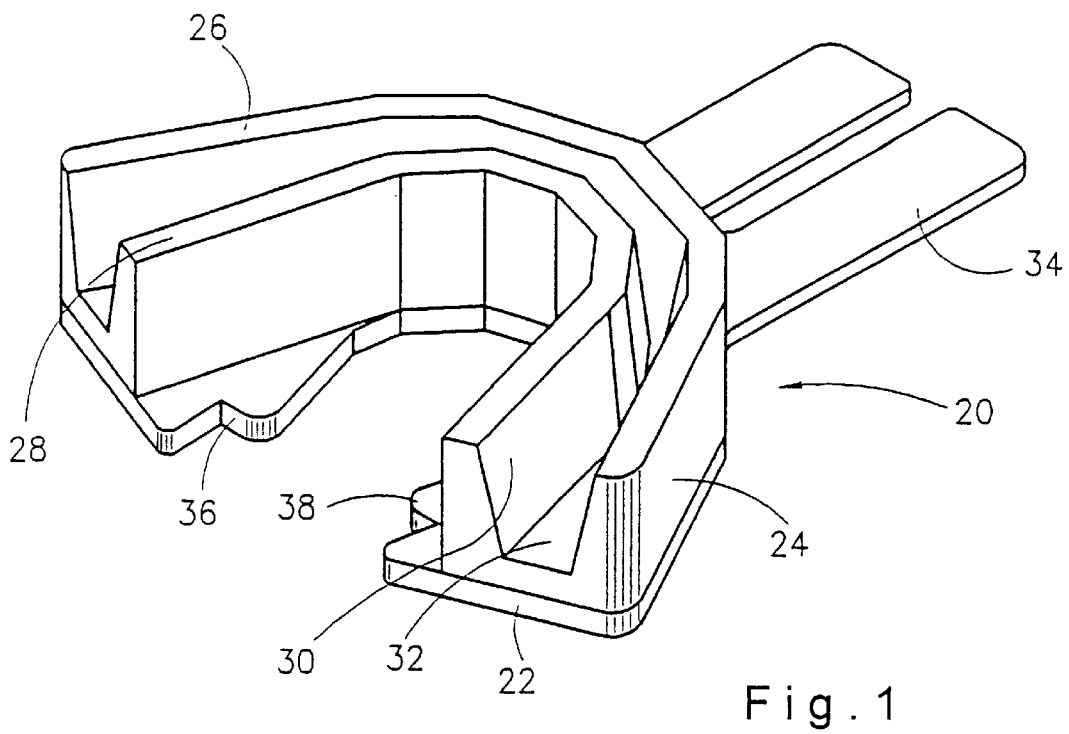
FIG. 1 is an isometric view of a tool in accordance with an embodiment of the invention, for obtaining a fill impression of the teeth of either the upper or lower jaw.

Reference is first being made to FIG. 1 showing a tool 20 in accordance with an embodiment of the invention. Tool 20 has a general shape resembling trays used hitherto in the art for obtaining teeth images. Tool 20 comprises a base 22 which is made of a rigid material such as metal, plastic or the like, which holds a matrix retainer 24 and having an outer wall portion 26 and inner wall portion 28 defining between them a trough-like recess 30. Matrix retainer 24 has a general "C"-like shape which approximates the shape of the teeth arrangement in the jaw.

Trough 30 has a shape allowing accommodation of all teeth in a jaw, in their entirety (when trough 30 is fitted over the teeth, the apex thereof will touch or be in close proximity to the bottom 32 of the matrix retainer, and the base of the teeth will be at about at the level of the upper surface of wall portions 26 and 28). The inner walls of recess 28 will typically have a rough or porous surface to allow firm attachment of the impression matrix thereto.

As can also be seen in FIG. 1, base 22 has a rearward expanding, fork-like member 34, and two internally directed projections 36 and 38. Member 34 and projections 36 and 38 are employed to fasten tool 20 within a slice cutting and image acquisition device, such as that which will be shown below with reference to FIGS. 11–13.

Figure 2:
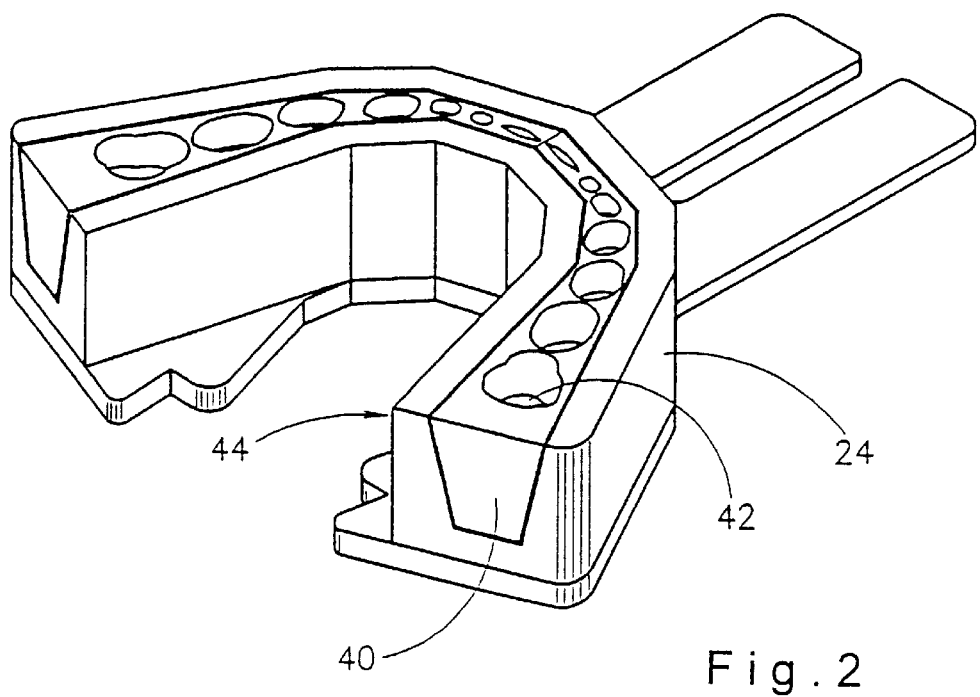
FIG. 2 shows the tool of FIG. 1 containing an impression matrix with a teeth impression fixed therein.
Figure 3:
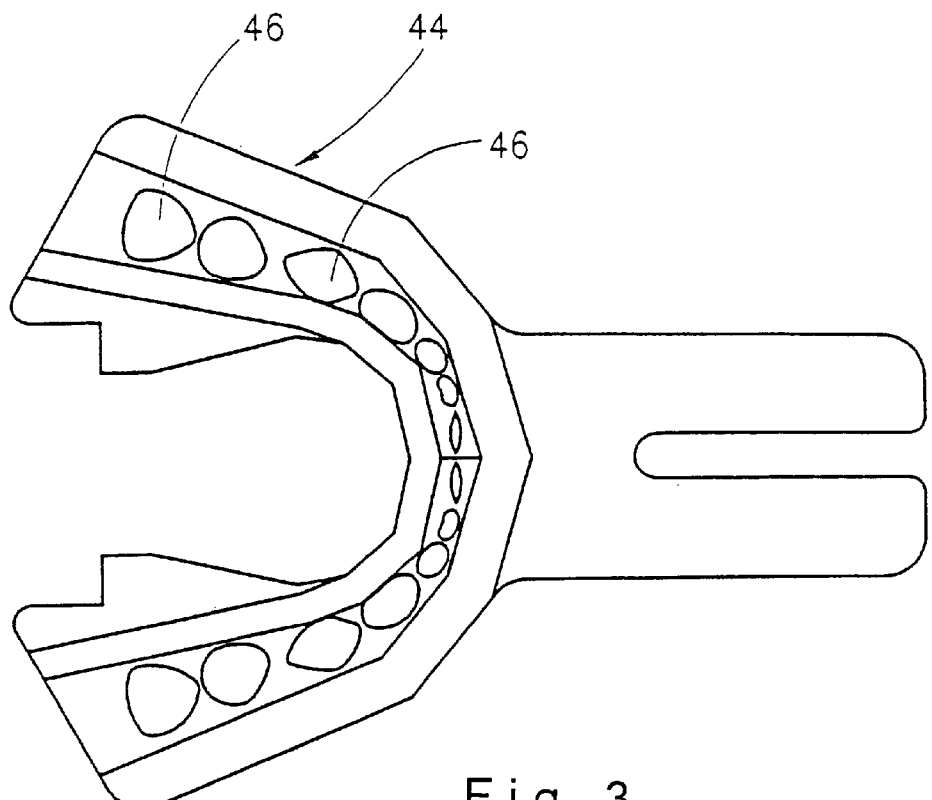
FIG. 3 is a plan view of the tool of FIG. 2.

In order to obtain a negative teeth model, an impression matrix is placed in recess 32, the tool is inserted into the mouth and the teeth are immersed in the impression matrix. As can be seen in FIG. 2, after curing of the impression matrix 40, a plurality of cavities 42, each corresponding to teeth, are fixed in the matrix. Upon curing of the impression matrix, an essentially integral block 44 is formed consisting of matrix retainer 24 and cured impression matrix with the negative teeth model 40. As can be seen in FIG. 3, when this integral block 44 is viewed from above the contours 46 of the cavities can be clearly seen.

In order to derive the teeth contours from the cured impression matrix, a chosen face of the matrix, which is typically the one corresponding to the teeth apex (it is possible, however, to choose also any other face of the matrix) is first levelled by removing a slice off this face to yield an essentially flat surface. An image is acquired, and then consecutive layers are sliced off, after each slicing an image is acquired again. The slicing operation, according to one embodiment, is shown schematically in FIG. 4A. Tool 20 with block 44 is placed in a plane and then moved in the X-direction, indicated by arrow 46, against blade 48. As will be appreciated, rather than moving tool 20, it is also possible to move blade 48 in the opposite direction. When tool 20 crosses the path of blade 48, the upper surface of tool 20 is leveled. At this stage, a first image can be acquired from the upper face of the block, and then tool 20 is moved upward by a small increment, e.g. 0.15 mm, as represented schematically by arrow 49, and then moved again towards blade 48 whereby a layer is sliced off from the upper surface and another image of a deeper layer of the matrix can be acquired, the image at this point corresponding to a level somewhat closer to the teeth apex.

Here again, it can be appreciated that rather than elevating block 20, it is possible also to lower blade 48, in similar increments.

Figure 4B:
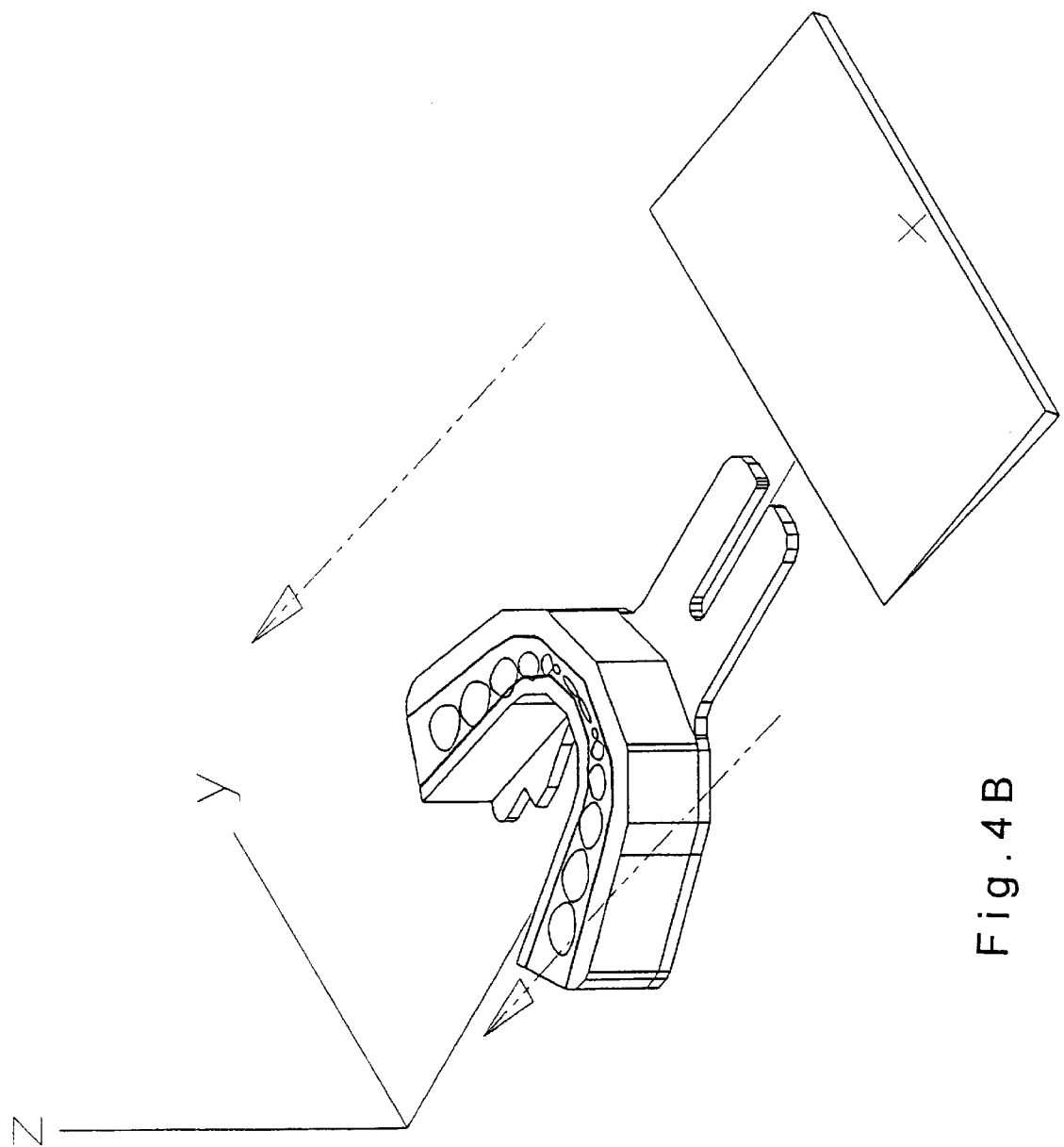
FIGS. 4B–4E are schematic representations of the manner of slicing off layers from the block in different orientation than that of FIG. 4A.
Figure 4C:
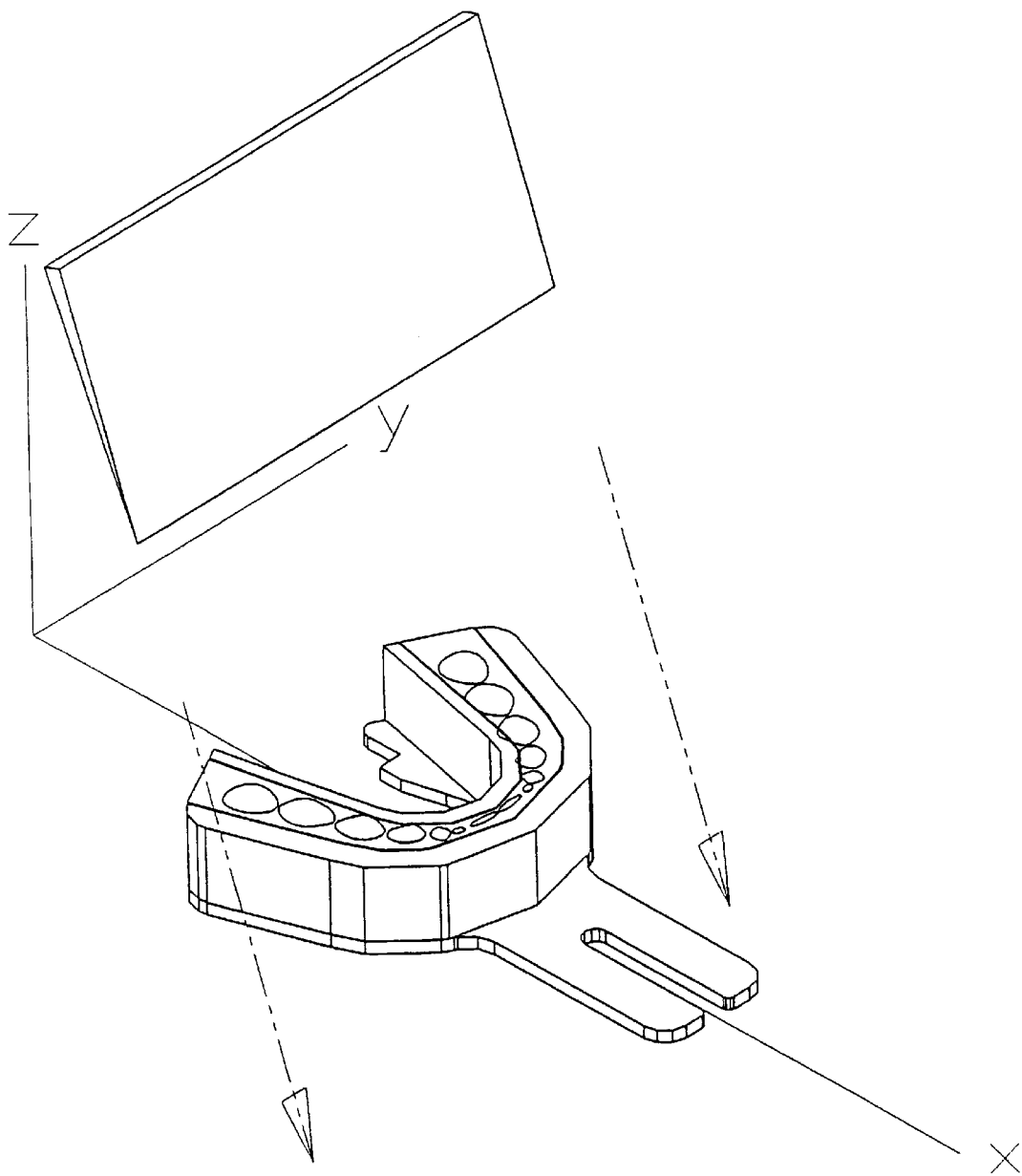
Figure 4D:
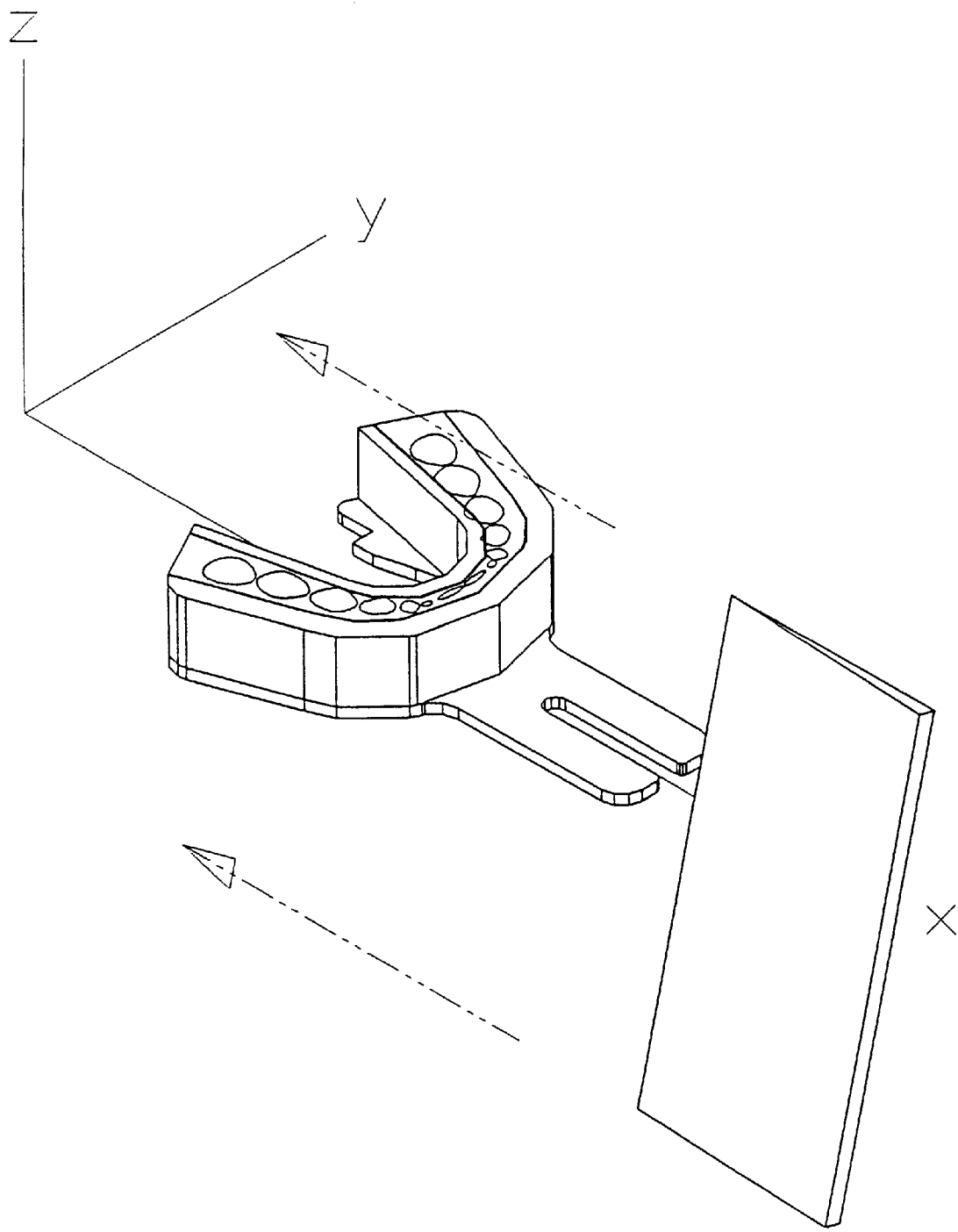
Figure 4E:
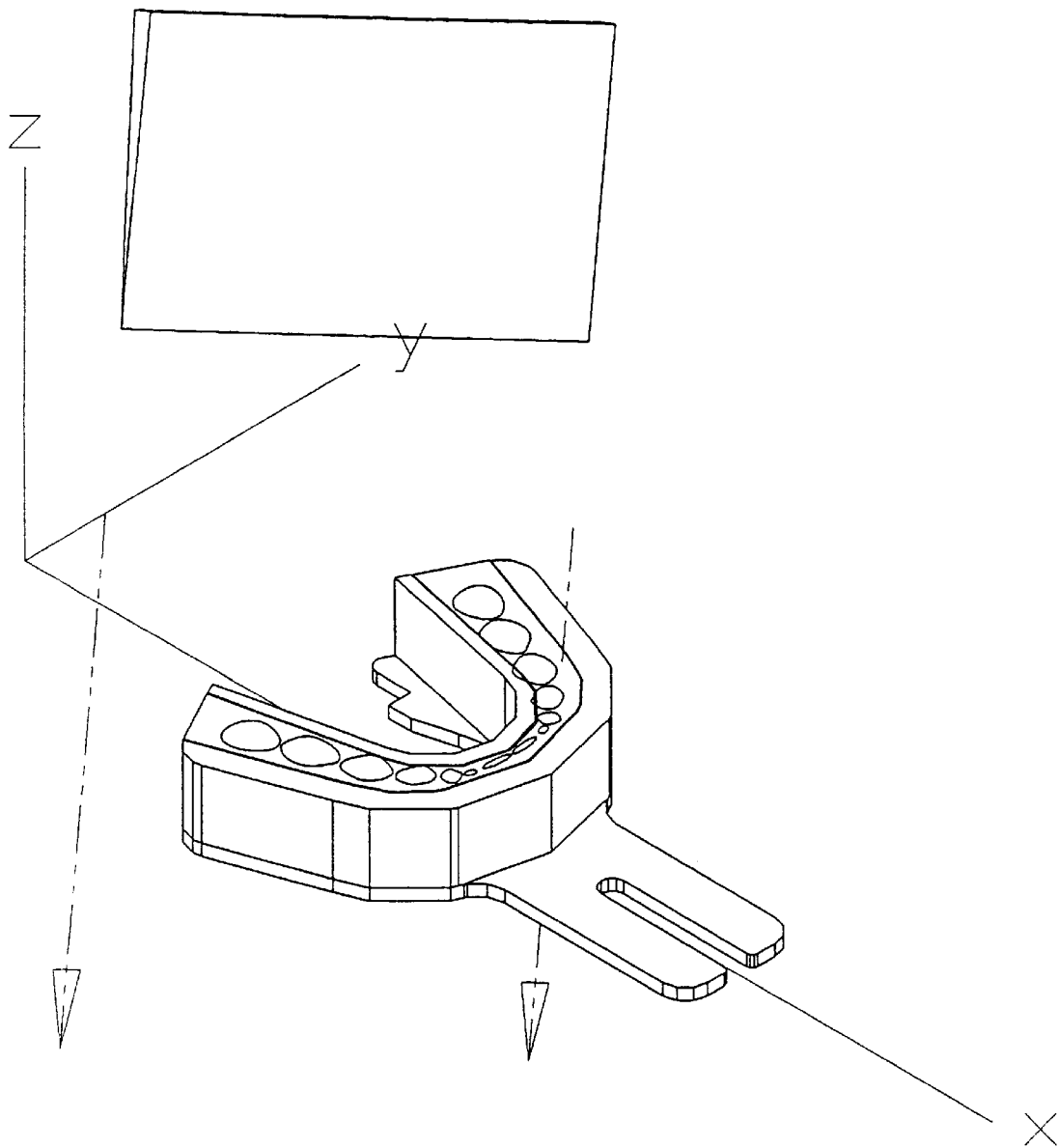

In FIG. 4A, the layers which are sequentially removed from block 44 are horizontal, i.e. in an orientation corresponding to base 22. However, it is possible to slice off layers also in orientation other than horizontal and several non limiting examples can be seen in FIGS. 4B–4E. In FIG. 4B, the blade cuts a layer off the block in a slanted, off-horizontal orientation; in FIG. 4C, the cutting of slices off the block is in a downward slanted orientation; in FIG. 4D, the slicing of the block is with the blade positioned so as to remove different layers starting from one side of the block; and in FIG. 4E, the blade is oriented such that it cuts off vertical layers which are angled vis a vis the longitudinal axis (X-axis) of the block. It will be appreciated that in FIG. 4B–4E, also the base of the block will be eventually cut thus meaning that the base, in such embodiments, has to be made of a substance which can be cut by the blade. Against this, in FIG. A, where the slicing is in parallel to the base, the base can also be made from a hard substance, e.g., metal.

FIG. 5 depicts a tool 50, (e.g. disposable impression tray made of styrofoam, commercially available from 3M unitek, U.S.A.) in accordance with another embodiment of the invention, tool 50 consists of a matrix retainer 51 and a handle 52 by which the tool can be held during preparing of the teeth impression 53 and during further processing as described above. The slicing operations using this tool is similar to that shown in FIG. 4A. For that purpose, tool 50 is placed on a block 54, e.g. by adhering the tool to the block, or placing it into a matching recess 55 adapted to slightly receive the bottom end of tool 50. Obviously block 54 is mechanically coupled, in a known per se manner, to table 104 (in FIG. 11—see below) or table 138 (in FIG. 16A—see below).

Figure 6:
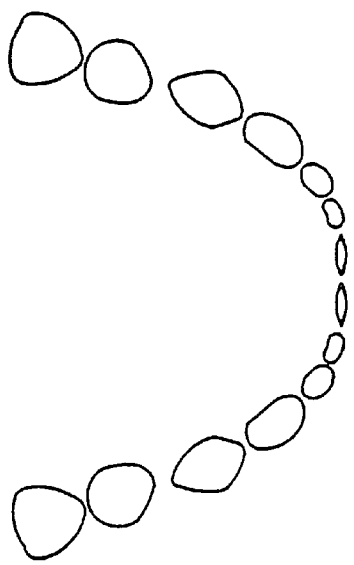
FIG. 6 shows the acquired teeth contours.

Following image acquisition and, straightforward image processing, teeth contours such as those shown in FIG. 6, are obtained, and a plural of such contours are used to obtain a dental image.

For various applications it is sufficient to obtain only a partial dental image, e.g. lingual image or buccal image. This is the case, for example, for monitoring of an orthodontic treatment, where usually the buccal face of the teeth is covered by braces, and accordingly it is possible to obtain an impression of only the other face. Furthermore, it is not always necessary to get a complete teeth impression and as teeth shape does not chance, in order to gain information on the teeth geometry and the relative teeth position, it is sufficient to obtain an impression of only the lingual on the buccal teeth faces.

Figure 7:
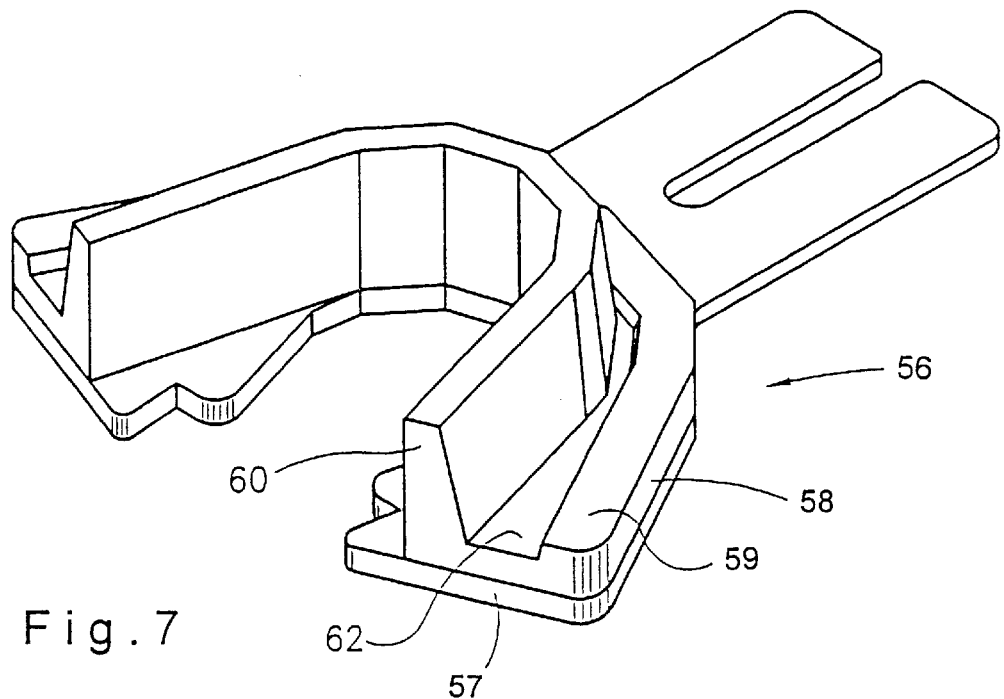
FIG. 7 is an isometric view of a tool in accordance with an embodiment of the invention for obtaining an impression of lingual teeth parts.

Reference is now being made to FIG. 7 showing a tool 56 suitable for obtaining a lingual teeth image. Tool 56 has a base 57, which is essentially the same as base 22 of tool 20 (FIG. 1). This tool differs however from tool 20 in matrix retainer 58 which in accordance with this embodiment has two unequal wall portions 59 and 60, external wall portion 59 being lower than internal wall portion 60. In use, impression matrix is placed within trough 62 and then the tool is placed in the mouth so that wall portion 60 presses against the lingual surfaces of the teeth.

Figure 8:
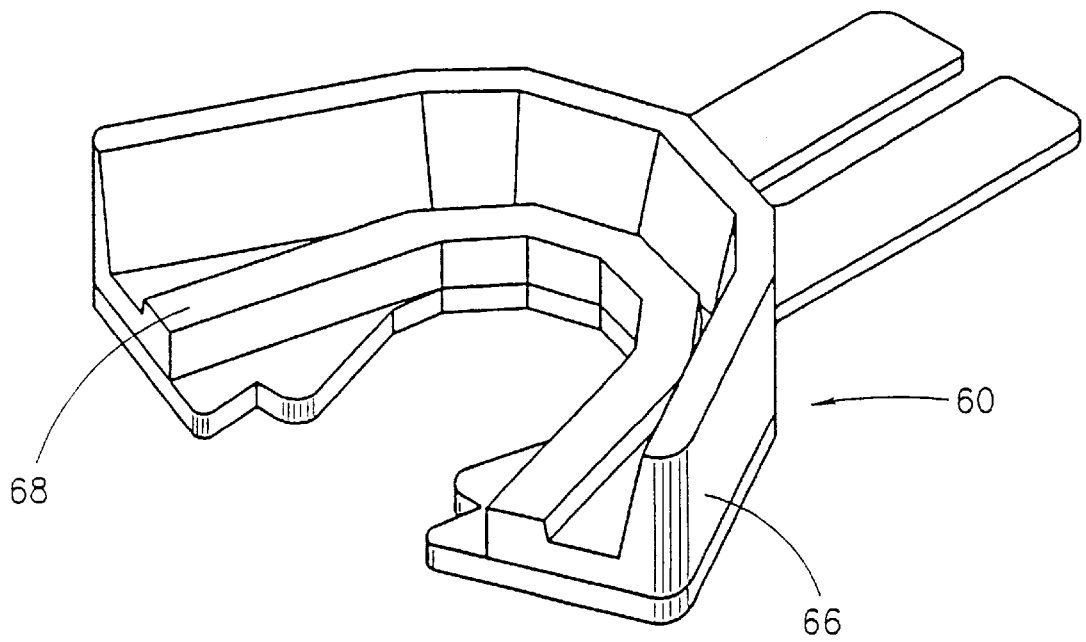
FIG. 8 is an isometric view of a tool in accordance with an embodiment of the invention for obtaining an impression of buccal teeth parts.

Tool 64 shown in FIG. 8, is similar in principle to tool 52 of FIG. 7 with the difference being that it is intended for obtaining an image only of the buccal teeth surfaces. External wall portion 66 is higher than internal wall portion 68 and in order to obtain a buccal image, a similar procedure to that used in connection with tool 52 is used here, mutatis mutandis.

Figure 9:
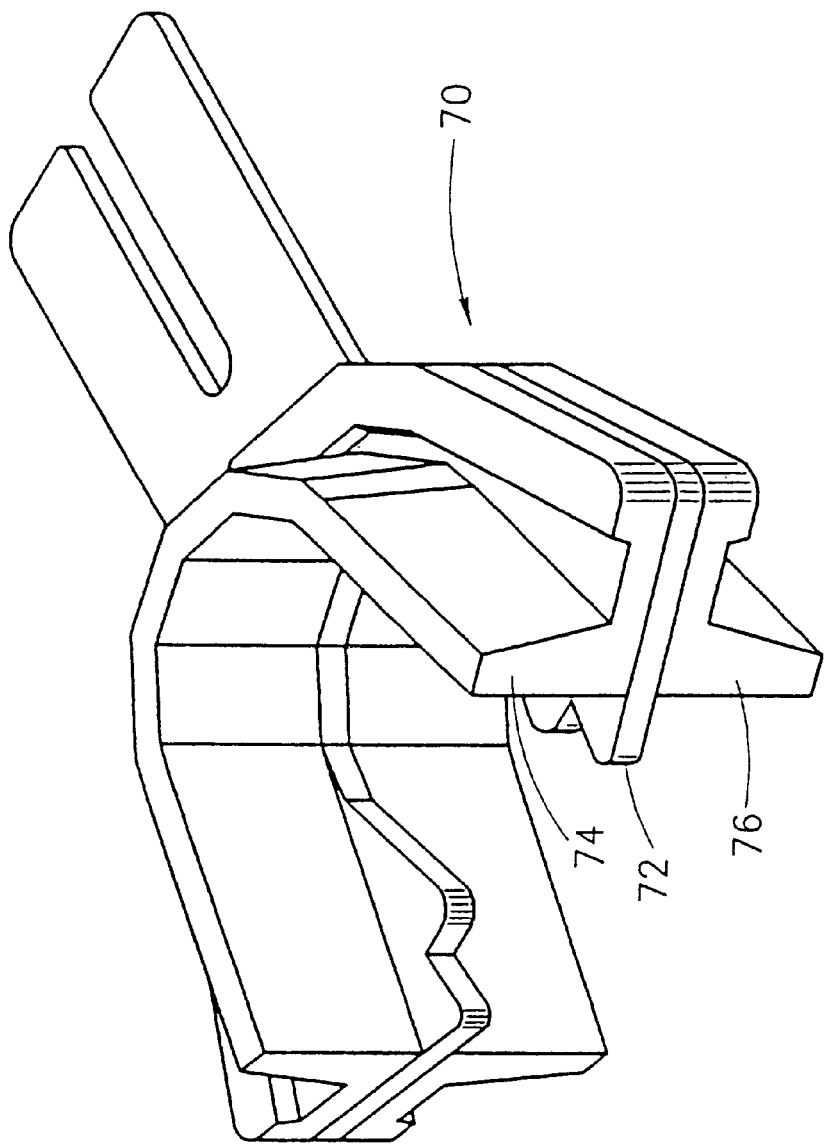
FIG. 9 is an isometric view of a tool in accordance with an embodiment of the invention useful for simultaneously obtaining of a negative impression of lingual surfaces of the teeth of both the upper and lower jaws.

Reference is now being made to FIG. 9 which illustrates a tool for obtaining a teeth impression 70 having a base 72 with two opposite impression matrix retainers 74 and 76 fixed to the upper and lower faces of the base, respectively.

Each of retainers 74 and 76 is essentially the same as retainer 56 of tool 52 shown in FIG. 7. Tool 70 in accordance with this embodiment is useful for obtaining simultaneously dental image of the lingual surfaces of both the upper and the lower jaws. It should be noted, however, that tool 70 is suitable for obtaining such simultaneous teeth impression where the teeth of the upper jaw and those of the lower jaw are essentially overlapping one another, or where there is only a slight shift between these two sets of teeth. In some individuals, there is a considerable distance between the two sets of teeth, and as the artisan can no doubt appreciate, it may at times be necessary to use an adjustable tool, where the matrix-holding member of the upper and the lower surfaces can be shifted one versus the other, to allow simultaneous accommodation of such shifted sets of teeth.

In various orthodontic treatments, the aim is to change the position or orientation of the teeth. A tool such as tool 60 shown in FIG. 7 is particularly suitable to obtain an image of the initial position and to allow monitoring of the progress of treatment.

Figure 10:
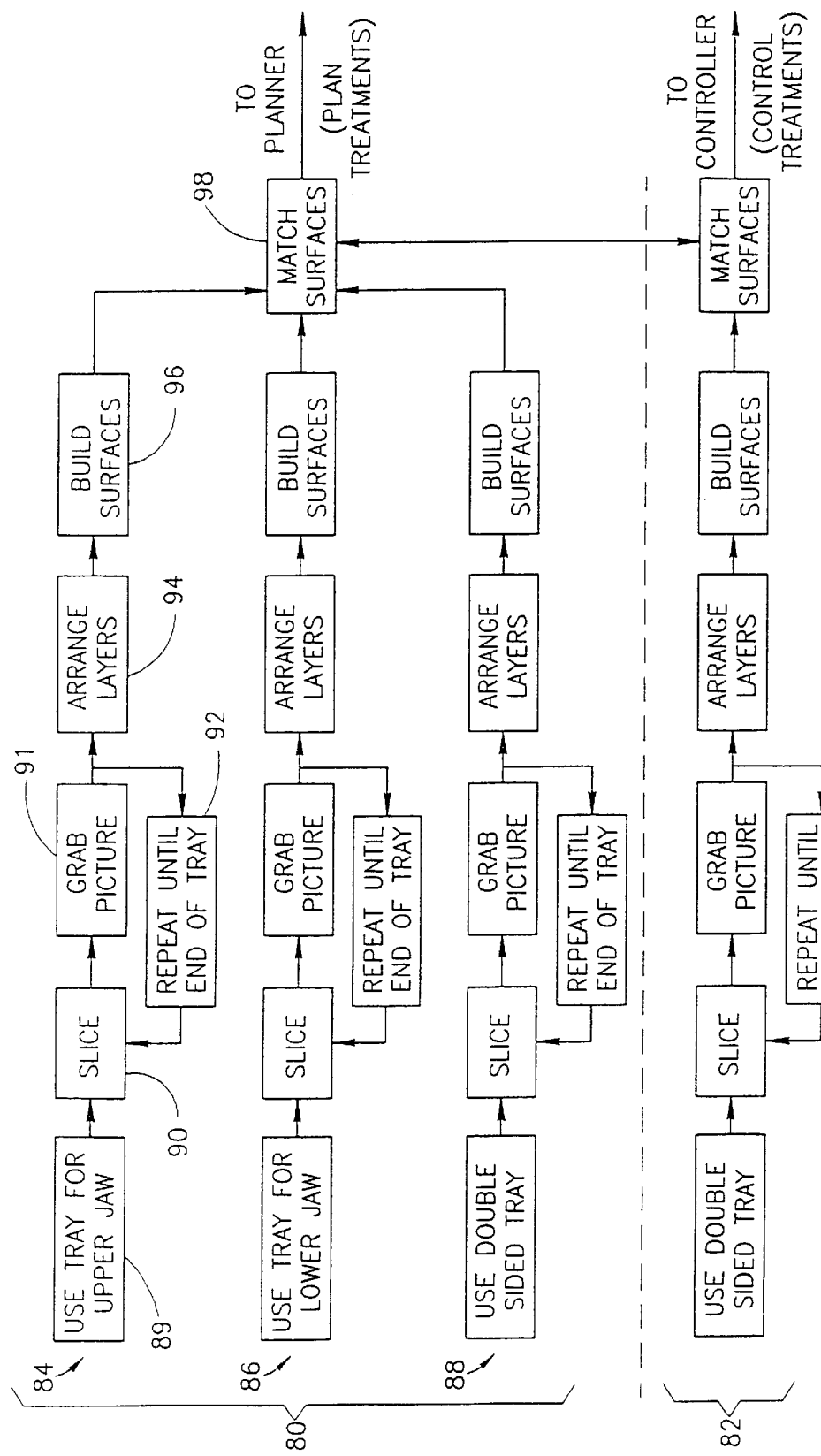
FIG. 10 is a simplified block diagram of the sequence of operation in performance of the method in accordance with the invention.

FIG. 10 shows a simplified block diagram of a typical manner of carrying out the method of the invention. The upper portion 80 relates to first-time image acquisition; the lower portion 82 relates to a periodical follow-up. Upon first-time image acquisition, e.g. prior to the onset of orthodontal treatment, a full image of the upper jaw 84, of the lower jaw 86 and of the relative positions of the teeth, both rows simultaneously 88, is acquired (the two former images are acquired by the use of a tool such as that shown in FIG. 1; the latter image is acquired by the use of a tool such as that shown in FIG. 7). Each image acquisition follows essentially the same sequence of operation, and accordingly the entire image acquisition process will be described simultaneously for acquiring of all three images.

Upon obtaining of a negative teeth model 89 by the use of the appropriate tool, the tool with the impression matrix having a teeth impression is placed in a device which is capable of cutting away thin slices from the matrix and acquiring a teeth impression image. The sequence begins by removing a slice 90 off the upper surface and then acquiring the first image 91. The sequence of slicing of an upper layer from the matrix block and acquiring an image is repeated, as represented by box 92, until sufficient layers have been removed. The individual images which have been acquired during the repeated steps 92, are then digitally processed 94 within a processor to allow for construction of a three-dimensional teeth image 96. The processor then combines the three individual images into one full dental image 98. The dental image thus obtained can then be used to plan the appropriate treatment, design braces for the individual, design bridges, crowns, shape of implants, etc.

Within the framework of monitoring of the treatment progress, it is sufficient to acquire only the lingual surfaces of the teeth. The actual image provides information on the teeth position and orientation, and as-the teeth three-dimensional structure does not change, there is no actual need to obtain a complete teeth image. Thus, for a follow-up, a tool such as that shown in FIG. 7, may be used. The sequence of the image acquisition proceeding will be similar to that described above with respect to first-time image acquisition.

Figure 11:
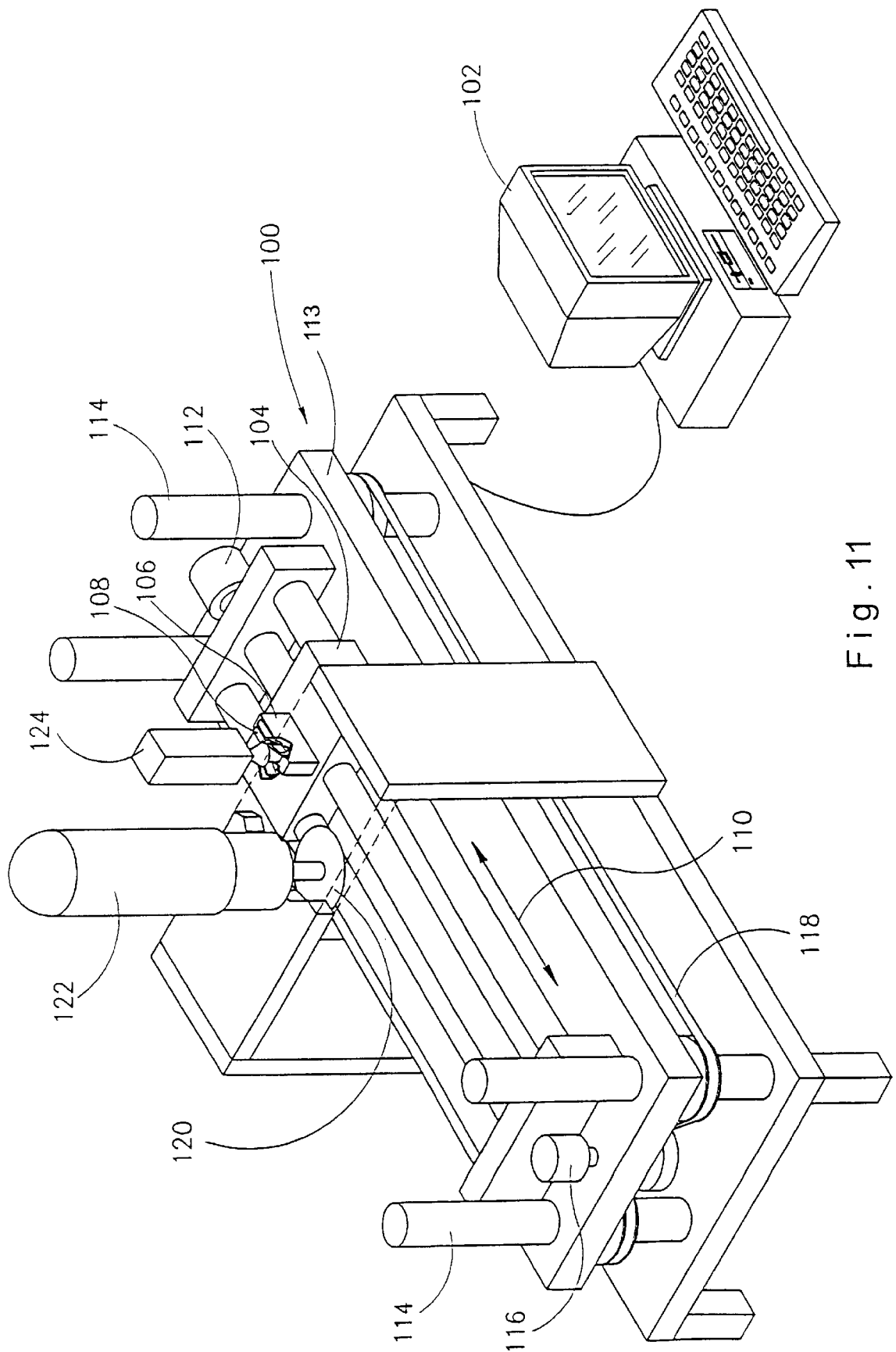
FIG. 11 is a simplifies isometric view of a system in accordance with an embodiment of the invention.
Figure 12:
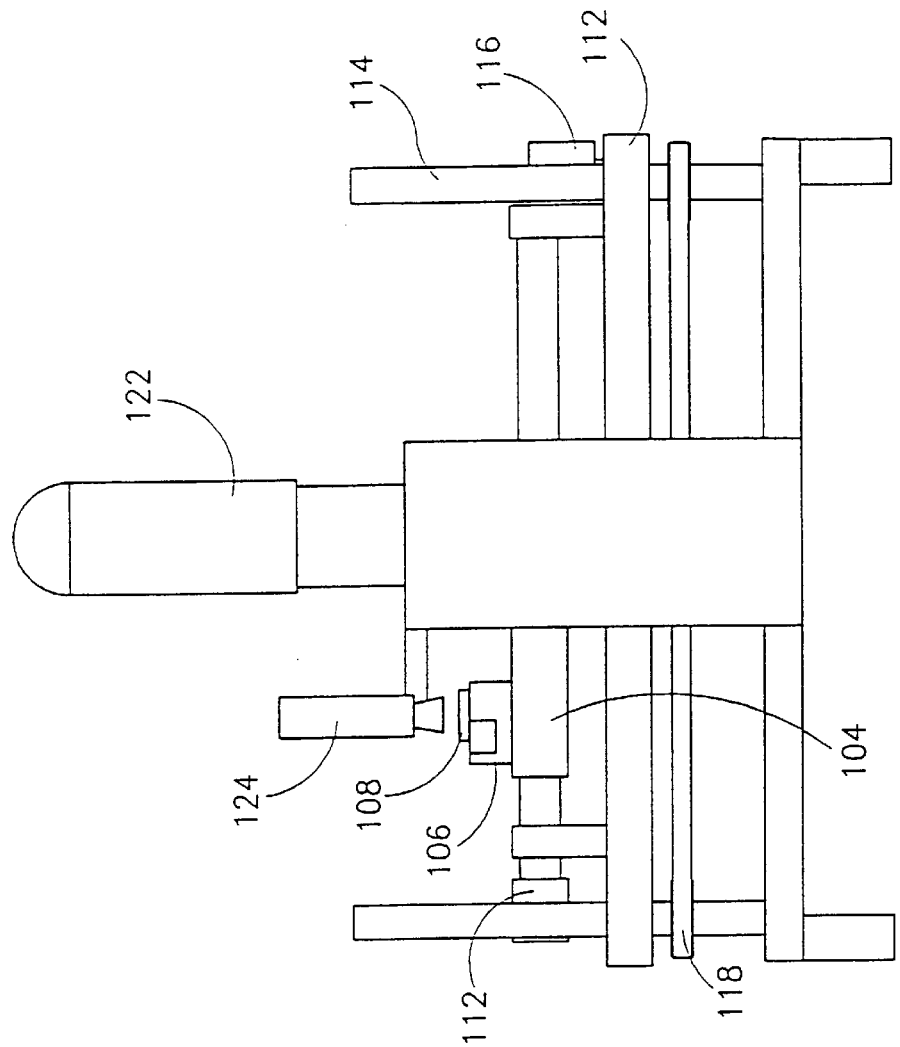
FIGS. 12 and 13 are, respectively, side and front views of the device shown in FIG. 10.
Figure 13:
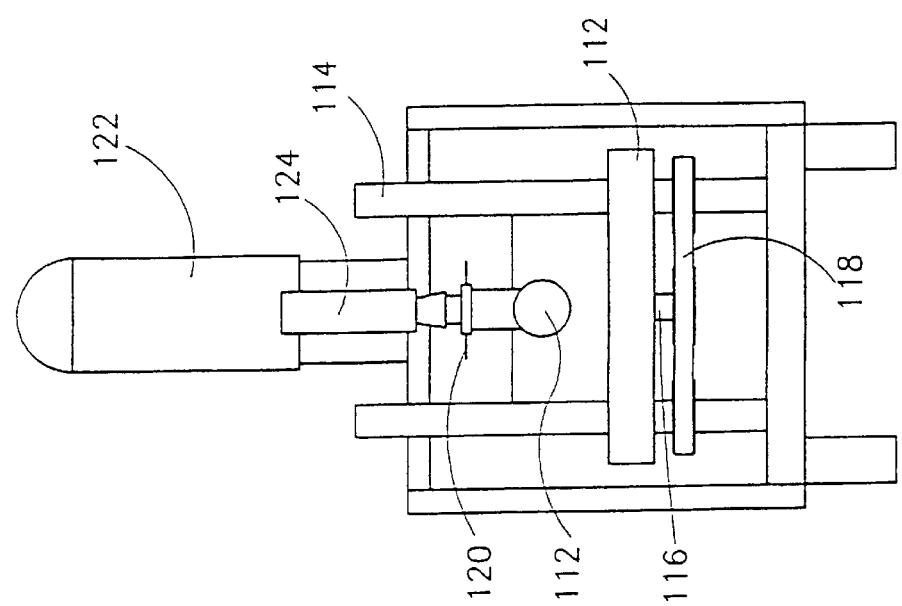

Reference is now being made to FIGS. 11–13 showing a system in accordance with an embodiment of the invention, for acquiring a dental image. The system comprises a slicing image acquisition device 100 and a computer 102. Device 100 comprises table 104 having a stage 106 which holds an impression tool 108, which may be a tool such as that shown in FIGS. 1, 7, 8 and 9. Table 104 can reciprocate in a longitudinal (X) direction, represented schematically by means of arrow 110 in FIG. 9, this reciprocating movement being actuated by means of electric motor 112. The entire structure comprising table 104 is held on a table 113. Table 113 is supported having threaded portions (not shown) on four support members 114, each one of which is rotatable. The rotation of support members 114 is powered by electric step motor 116, which transfers the force to all support members by means of transmission belt 118. The rotation of each of support members 114, depending on the direction, will either elevate or lower table 113.

Device 100 further comprises a rotatable blade 120 powered by spindle motor 122 and comprises a video camera 124 situated above tool 108 when table 104 is in its retracted position as shown in FIGS. 11 and 12.

The operation of motors 112, 116 and 122 is controlled by computer 102, which is also linked to video camera 124 and thus receives and can then process image acquired thereby.

After fastening tool 118 on to stage 116, and after optionally filling the impression cavities or recesses with a dye or applying color to the walls of the impression or cavity, a first image may be acquired by camera 124. The table 104 is then pushed forward whereby the upper surface of the block on tool 98 (the block including the matrix and the support member held on the tool) crosses the path of blade 120 and consequently an upper layer thereof is sliced off. Upon retraction of table 104 and bringing it back to the position shown in FIGS. 11 and 12, a second image may then be acquired by camera 124. Step motor 116 is then rotated and elevates table 112 by one predetermined step and then the sequence of slicing of an upper layer and acquiring an image is then repeated. The sequence is repeated, typically until the entire block has been sliced off. Then motor 116 lowers table 112 to the initial position whereby the sequence can then be repeated again with a new matrix holding tool.

It should be noted that, rather than changing the relative vertical position of table 104 and blade 120, in a manner as described hereinbefore or in any other manner, it is also possible to stepwise lower blade 110.

Figure 14:
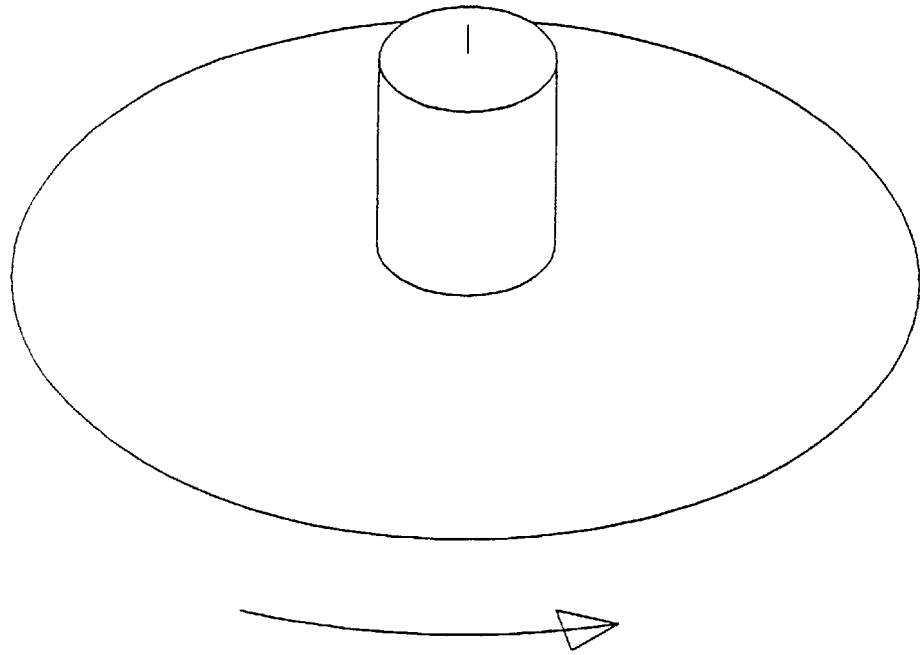
FIGS. 14A–E are schematic representations of general embodiments of tools for cutting off layers from teeth models in different orientations.
Figure 14:
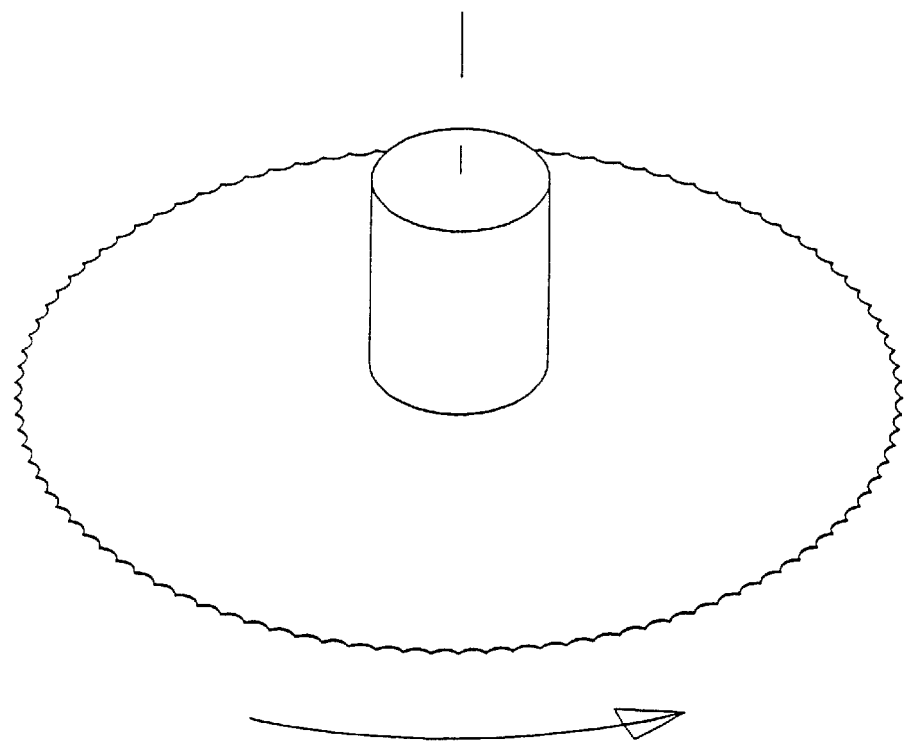
Figure 14:
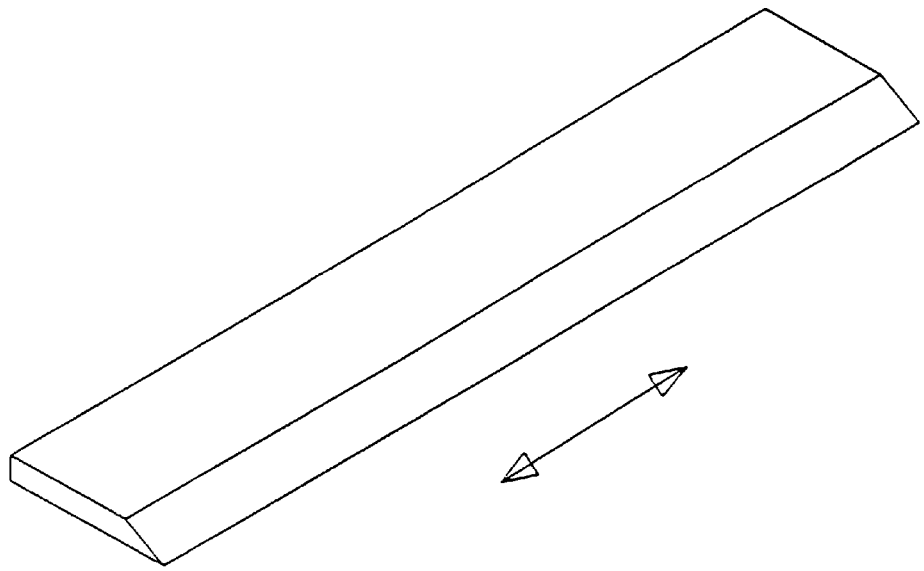
Figure 14:
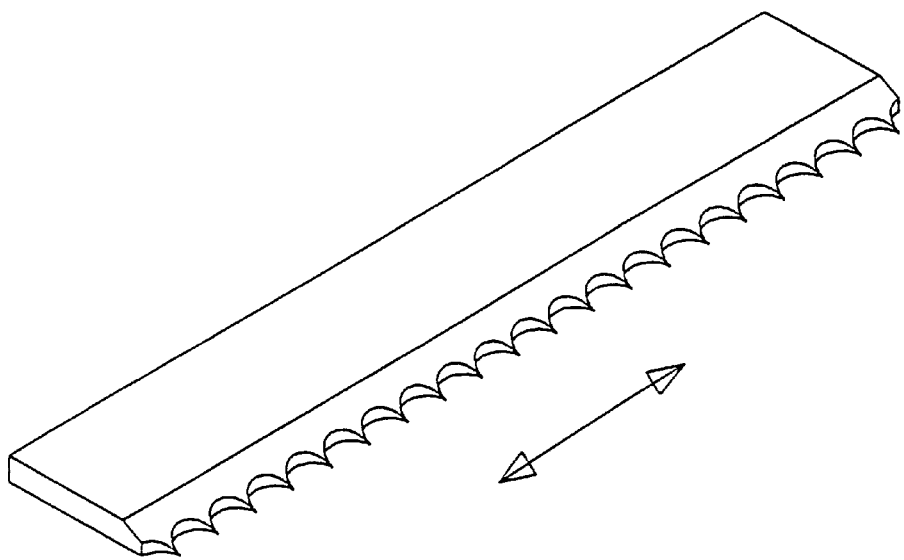
Figure 14:
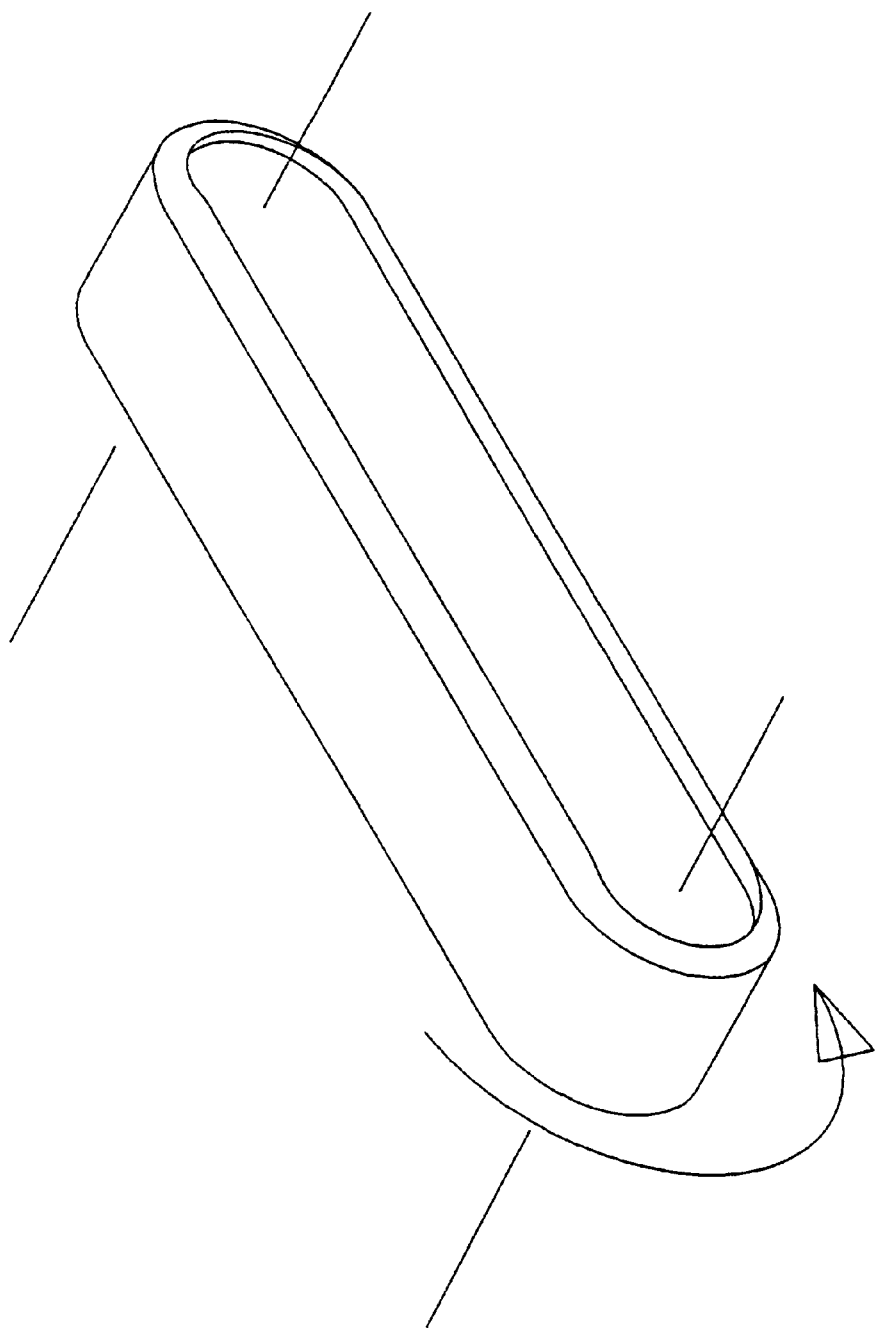

Device 100 in FIG. 11 makes use of a rotatable blade 120 but as will be appreciated by the artisan, a variety of other types of blades may also be used. Example of such blades can be seen in FIG. 14A–E. The blade in 14A is a turning blade with a straight edge similar to that used in device 110. The blade in FIG. 14B is a turning blade with a jagged edge; but in FIG. 14C it is an oscillating blade with straight edge; and in 14D is an oscillating blade with a jagged edge; the blade in FIG. 14E is a rotating band with a straight edge.

Computerized techniques and algorithms for generating the geometry of three-dimensional object from consecutive two-dimensional representations of contours of the object at different latitudes, are generally known per se. See for example the following publication which is incorporated herein by reference: "Building, Visualizing, and Computing on Surfaces of Evolution", H. Harlyn Baker, SRI International, Jul. 1988, page 31.

Figure 15:
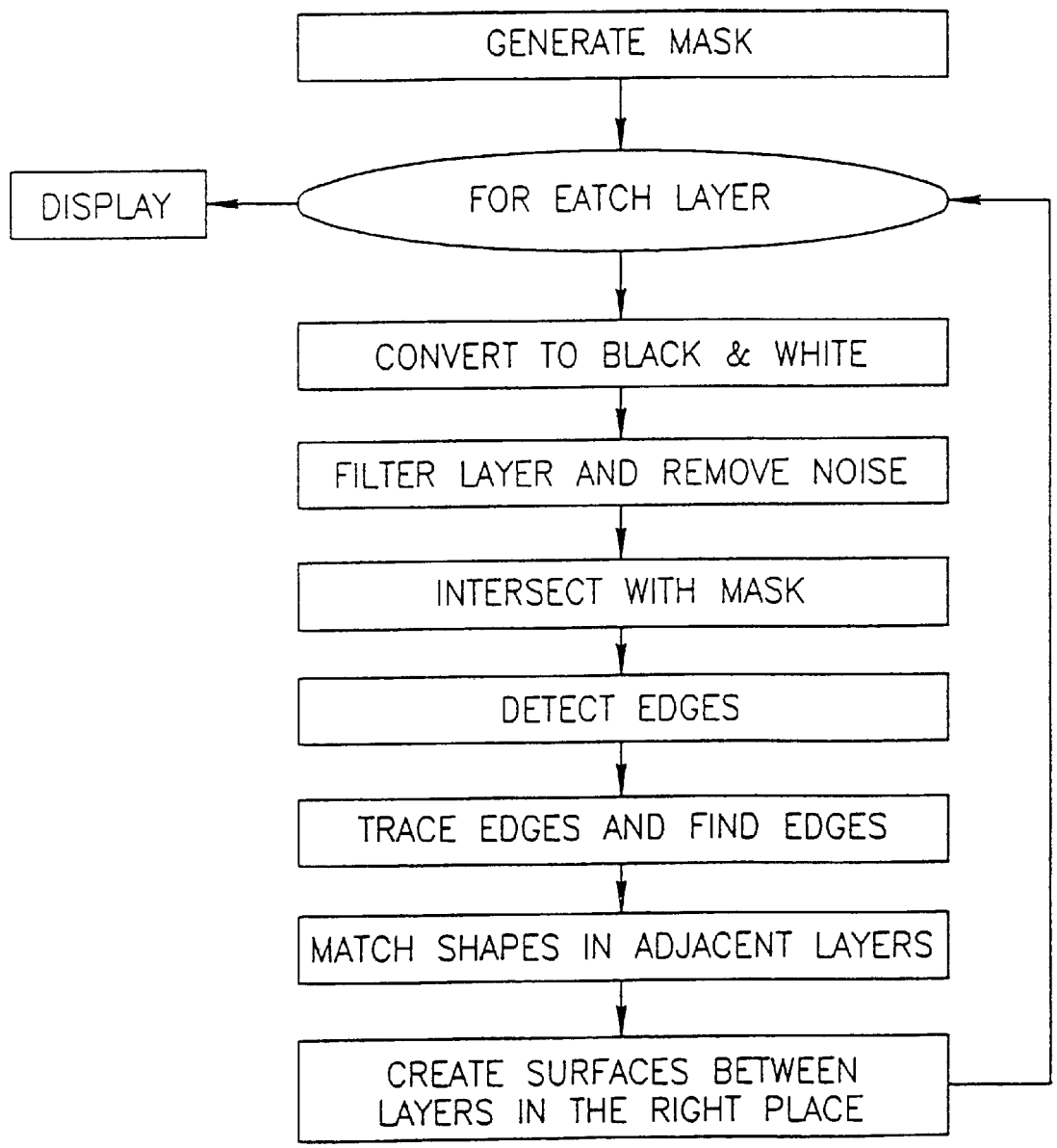
FIG. 15 shows a typical block diagram for combining the two-dimensional acquired images to a three-dimensional dental image.

A typical, yet not exclusive algorithm which can be used in accordance with the invention for combining the consecutive contours into a three-dimensional teeth representation is shown in FIG. 15, which is self-explanatory for those skilled in the art in view of the aforementioned reference and the available knowledge.

Regardless of the embodiment under consideration, in order to obtain an accurate constructed three dimensional image, it is, desired to ensure the alignment of consecutive acquired two-dimensional images, i.e. that they are not shifted one with respect to the other.

Figure 16:
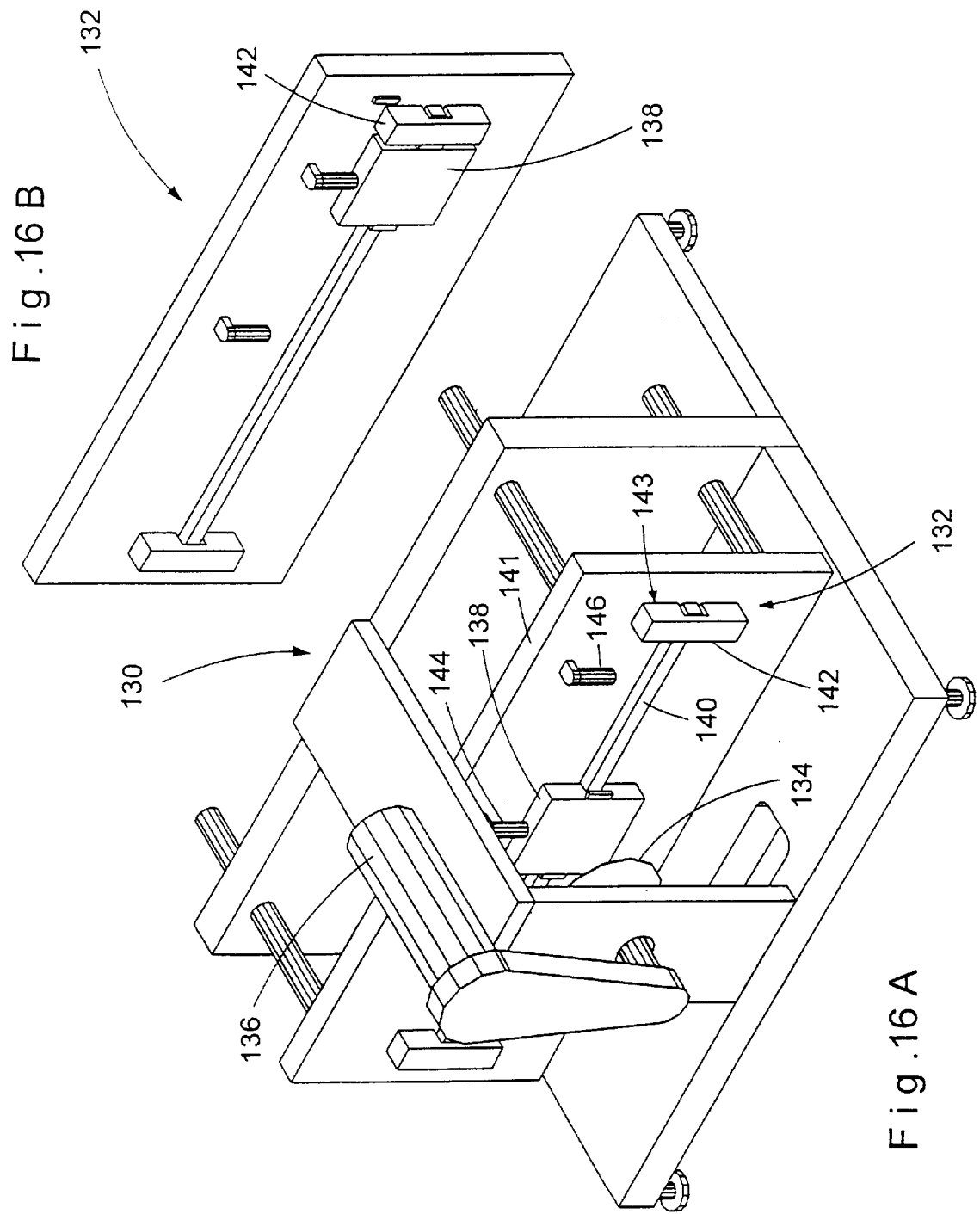
FIG. 16A is a schematic representation of a tool in accordance with an embodiment of the invention which includes an alignment mechanism for alignment of acquired two-dimensional images.
FIG. 16B is a separate view of the alignment mechanism that forms part the tool of FIG. 16A.

Attention is now directed to FIG. 16A and 16B, showing a typical, yet not exclusive, example of a tool 130 which includes an alignment mechanism 132. For clarity, all the parts of tool 130 which are not essential for illustrating the alignment mechanism are removed. Nevertheless, it should be noted that tool 130 albeit drawn in a horizontal orientation, resembles to a large extent, the tool 100 shown in FIG. 11 which is drawn in vertical orientation.

As shown, rotatable blade 134 is powered by motor 136. Table 138 is capable of reciprocating in a longitudinal X direction along sliding rod 140. Although not shown in FIG. 16A, table 138 carries a stage and the impression tool, e.g. of the kind indicated by reference numerals 106 and 108 in FIG. 11. As explained before after fastening the tool and the stage onto the table, and after optionally filling the impression cavities or recesses with a dye or applying color to the walls of the impression or cavity, a first image may be acquired by the video camera. Although not shown in FIG. 16A, the camera is situated opposite the table 138 when the latter is in the extreme right position, as depicted in FIG. 16B.

Table 138 is then pushed forward whereby the upper surface of the block (the block including the matrix and the support member held on the tool—not shown) crosses the path of blade 134 and consequently an upper layer thereof is sliced off. Upon retraction of table 138 and bringing it back to the position shown in FIGS. 16B, a second image may then be acquired by the camera. The alignment mechanism assures that the second image is in alignment with the previous one.

Turning now to the specific structure of the alignment mechanism, it includes a bumper 142, mounted on table 141, and having a flat lateral 143 face for stopping the motion of table 138 in the right direction. The table, in its extreme right position is pressed against the lateral face of the bumper thereby ensuring that the table is retained in a fixed and the same position during consecutive image acquisitions. Since, as recalled, the stage and the impression tool are firmly fastened to the table so as to eliminate any movement thereof relative to the table and further bearing in mind that the camera is secured in a fixed spatial position, it readily arises that any two consecutive acquired images are aligned one with respect to the other.

Figure 17:
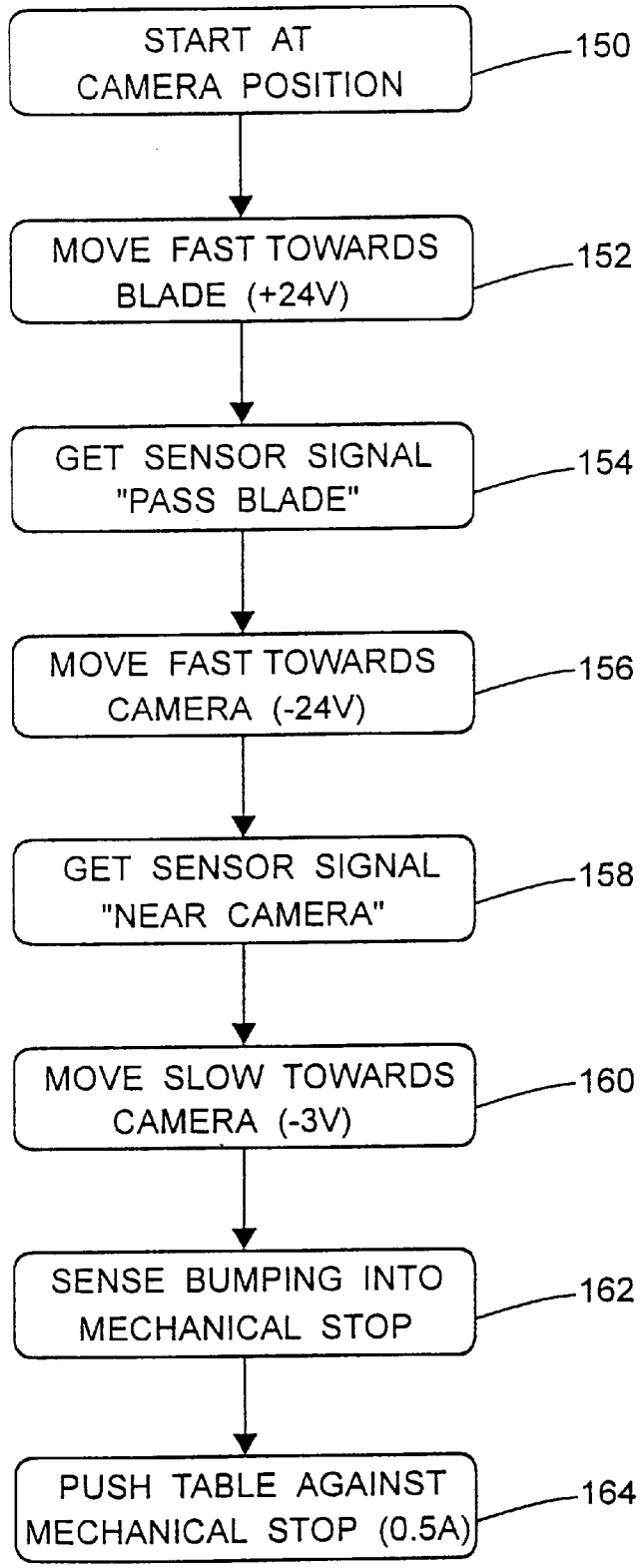
FIG. 17 shows a typical block diagram of the electrical control associated with the alignment mechanism.

The pertinent electrical control operations, which are known per se, are described generally with reference also to FIG. 17. Thus, and shown in step 150, a first image is acquired when the table is situated in the extreme right position (FIG. 16B). Having acquired the image, and as shown in step 152, the table 138 is moved fast along the sliding rod 140 towards the blade by applying high voltage (+24V) to the motor (not shown in FIG. 16A). As the table pass the blade and the upper layer of the impression is sliced off, the table approaches a sensor 144 that is fixedly attached to table 141 (e.g. a known per se and commercially available proximity switch) and cause the sensor to generate an electric signal indicative of a "pass blade" state (step 154). Preferably, responsive to the specified electrical signal, the table 138 is slightly lowered by means of step motor (not shown in FIG. 16A) in order to avoid undesired friction between the blade and the impression as the table moves fast in the opposite direction towards the camera. Having lowered the table, the polarity of the DC voltage that is applied to the motor is inverted (−24V) which results in fast movement of the table towards the camera (step 156). When the table 138 traverses sensor 146 which is also fixedly attached to table 141, the sensor (being, for example, the specified proximity switch) generates an appropriate electric signal indicative of a "near camera" state (step 158). Responsive to the generation of the electric signal, the DC voltage that is applied to the motor is attenuated (e.g. −3V) which results in a slower movement of the table towards bumper 143 (step 160). As the table bumps the stopper 141 the load on the motor spindle is increased which results in an increase in the electrical currency that is supplied to the motor. A suitable, known per se, control circuitry (not shown) senses the increase in currency (step 162) and limits the currency to e.g. 0.5A thereby ensuring an ongoing controlled pressure of the table 138 against the stopper 143 when the next image is acquired (step 164).

Thereafter, the step motor (not shown in FIG. 16A) is rotated and elevates table 141 by a predetermined extent and then the sequence of slicing of an upper layer and acquiring an image is repeated, typically, until the entire block has been sliced off.

What is claimed is:

1. A method for obtaining a dental image which comprises:

(a) providing a negative teeth model, of substantially all teeth of a jaw, comprising a matrix with a plurality of cavities or recesses with boundaries corresponding to boundaries of the teeth; the negative teeth model being held by a firm matrix retainer made of a substance which can be cut by a cutting tool which can cut the matrix;

(b) removing a layer portion off a face of choice, the face of choice being a face of the teeth model corresponding to the teeth apex or the teeth base, the layer being removed by said cutting tool so as to obtain a flat, surface, and acquiring a first, two-dimensional digital image of the flat surface or of the removed portion;

(c) removing another layer portion off the chosen face so as to obtain a new, flat surface and acquire a consecutive two-dimensional digital image of the new flat surface or of the removed portion;

(d) repeating step (c) a plurality of times until removal of sufficient layer portions of the teeth model to allow the obtaining of a dental image;

(e) determining boundaries of the cavities or recesses in the case of the negative teeth model in the first image and in each of the consecutive images to obtain a plurality of boundaries representations of the first and subsequent images;

(f) combining at least some of the boundaries' representations into a three-dimensional digital dental image; and coloring the boundaries of the teeth of model with a contrasting color or filling the cavities or recesses with a colored curable substance.

2. A method for obtaining a dental image which comprises:

(a) providing a negative teeth model, of substantially all teeth of a jaw, comprising a matrix with a plurality of cavities or recesses with boundaries corresponding to boundaries of the teeth; the negative teeth model being held by a firm matrix retainer made of a substance which can be cut by a cutting tool which can cut the matrix;

(b) removing a layer portion off a face of choice, the face of choice being a face of the teeth model corresponding to the teeth apex or the teeth base, the layer being removed by said cutting tool so as to obtain a flat, surface, and acquiring a first, two-dimensional digital image of the flat surface or of the removed portion;

(c) removing another layer portion off the chosen face so as to obtain a new, flat surface and acquire a consecutive two-dimensional digital image of the new flat surface or of the removed portion;

(d) repeating step (c) a plurality of times until removal of sufficient layer portions of the teeth model to allow the obtaining of a dental image;

(e) determining boundaries of the cavities or recesses in the case of the negative teeth model in the first image and in each of the consecutive images to obtain a plurality of boundaries representations of the first and subsequent images;

(f) combining at least some of the boundaries' representations into a three-dimensional digital dental image; and filling the cavities with a substance having a contrasting color.

* * * * *